United States Patent [19]
Kanamaru et al.

[11] Patent Number: 5,866,609
[45] Date of Patent: Feb. 2, 1999

[54] SUBSTITUTED VINYLUREA DERIVATIVES AND MEDICINE CONTAINING THE SAME

[75] Inventors: Yoshihiko Kanamaru, Tomisato-machi; Hiroyuki Hirota, Shisui-machi; Akihiro Shibata, Yachiyo; Teruo Komoto, Chiba; Hiroyuki Naito; Koichi Tachibana, both of Narita; Mari Ohtsuka, Narashino; Fumio Ishii, Sendai; Susumu Sato, Narita, all of Japan

[73] Assignee: SS Pharmaceutical Co., Ltd., Tokyo, Japan

[21] Appl. No.: 899,647

[22] Filed: Jul. 24, 1997

[30] Foreign Application Priority Data

Aug. 9, 1996 [JP] Japan .................................. 8-211265

[51] Int. Cl.$^6$ ........................ A61K 31/17; C07C 275/28; C07C 275/04
[52] U.S. Cl. .......................... 514/596; 514/255; 514/329; 514/464; 514/535; 514/564; 514/595; 514/598; 514/524; 544/386; 544/390; 544/391; 546/224; 549/434; 549/435; 560/34; 562/439; 564/48; 564/52; 558/417
[58] Field of Search ........................ 564/48, 52; 514/595, 514/596, 598, 535, 564, 464, 329, 255, 524; 560/34; 562/439; 549/434, 435; 546/224; 544/386, 390, 391; 558/417

[56] References Cited

PUBLICATIONS

Eiden et al, Arch. Pharm, No. 7, pp. 445–455, 1963.
Tawada et al, J.Med.Chem., vol. 37, pp. 1067–1083, 1994.
Maduskuie et al, J. Med. Chem, vol. 38, pp. 1067–1083, 1995.

*Primary Examiner*—Shailendra Kumar
*Attorney, Agent, or Firm*—Oblon, Spivak, McClelland, Maier & Neustadt, P.C.

[57] ABSTRACT

Disclosed herein are substituted vinylurea derivatives represented by the following general formula (1):

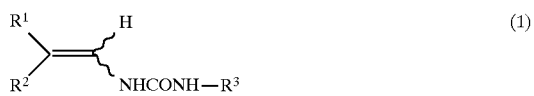

wherein $R^1$ and $R^3$ are independently a phenyl group which may be substituted, $R^2$ is a phenyl group which may be substituted, or a cycloalkyl group, and wave lines mean that the bonding state may be either E or Z, with the proviso that the cases where $R^1$, $R^2$ and $R^3$ are unsubstituted phenyl groups, and where $R^1$ and $R^2$ are unsubstituted phenyl groups and $R^3$ is a 4-ethoxyphenyl group are excluded, or salt thereof, and medicines comprising such a derivative as an active ingredient as well as a method of preventing and treating arteriosclerosis with such a medicine. The derivatives or salts thereof selectively and strongly inhibit ACAT in macrophages and are hence useful as prophylactic and therapeutic agents for arteriosclerosis.

14 Claims, No Drawings

SUBSTITUTED VINYLUREA DERIVATIVES AND MEDICINE CONTAINING THE SAME

BACKGROUND OF THE INVENTION

1. Field of the Invention

The present invention relates to novel substituted vinylurea derivatives or salts thereof, and medicines comprising such a derivative as an active ingredient as well as a method of preventing and treating arteriosclerosis with such a medicine, and particularly to substituted vinylurea derivatives or salts thereof, which are useful as anti-arteriosclerotic agents which selectively inhibit an acyl-coenzyme cholesterol acyl-transferase (ACAT) in macrophages present in an artery wall, thereby preventing formation of foam cells, and medicines comprising such a derivative as an active ingredient as well as a method of preventing and treating arteriosclerosis with such a medicine.

2. Description of the Background Art

Cardiac diseases and cerebrovascular diseases stand second and third, respectively, to cancers in Japan as regards the causes of death, and are more than half the number of the causes of death if both are put together. Most of these diseases occur as a terminal symptom of arteriosclerosis. The arteriosclerosis is also caused by aging and has no general diagnosis. Besides, the name of a disease called arteriosclerosis is also not present. However, it is considered that the mortality from arteriosclerosis is very high.

With respect to the mechanism attacked by arteriosclerosis, there have been many unknown points. Many researches have been conducted in this mechanism, and the mechanism has been rapidly elucidated in recent years. More specifically, when arteriosclerosis occurs, an atherosclerotic lesion, in which cholesterol esters are accumulated in plenty, is formed. With the growth of this lesion, the constriction of a vascular lumen progresses, resulting in complete obstruction of the vessel in the worst case. As described above, the arteriosclerosis is a very horrible disease. As a method for treating and preventing arteriosclerosis, a method of lightening risk factors dominates up to the present. This method is a method in which exacerbation factors participating in the attack of arteriosclerosis are removed. More specifically, in addition to dietetic therapy, there are many useful therapeutic and prophylactic methods such as methods of administering various kinds of serum lipid-reducing agents and antihypertensive drugs. However, the action of these drugs on arteriosclerosis is indirect, and so there is a strong demand for development of drugs which directly act on arteriosclerosis.

An ACAT inhibitor is one of the proposed drugs having such direct action. ACAT is an enzyme that acylates cholesteryl to synthesize an accumulation type cholesteryl ester. In the atherosclerotic lesion in arteriosclerosis, this cholesteryl ester is accumulated in excess. It is therefore expected that the inhibition of ACAT can prevent an excess of accumulation of the cholesteryl ester, and also the growth of the sclerotic lesion.

The conventional ACAT inhibitors include compounds described in Japanese Patent Application Laid-Open Nos. 117651/1990, 234839/1992 and 7259/1991, "H. Tawara et al., J. Med. Chem., 37, 2079–2084 (1994)", and Japanese Patent Application Laid-Open Nos. 41006/1996 and 258200/1995. These documents investigate inhibitory activities against ACAT in small intestine microsomes or liver microsomes, or an action that cholesterol in plasma is indirectly reduced, but do not describe anything about inhibitory activities against ACAT in macrophages that are considered to be more important when investigating an anti-arteriosclerotic action.

In compounds described in "Thomas P. Maduskuie, Jr. et al., J. Med. Chem., 38, 1067–1083 (1995)", those that more strongly inhibit ACAT in macrophages compared with ACAT in liver microsomes are also found. However, it cannot be said that their selective effects are sufficient.

SUMMARY OF THE INVENTION

Accordingly, it is an object of the present invention to provide compounds which particularly strongly and selectively inhibit ACAT in macrophages present in an artery wall among ACAT present all over the body, such as liver, gut mucosa, artery, adrenal, ovary and skin to prevent formation of foam cells, and are useful as medicines for preventing and treating arteriosclerosis.

In view of the foregoing circumstances, the present inventors have carried out an extensive investigation. As a result, it has been found that novel substituted vinylurea derivatives represented by the general formula (1), which will be described subsequently, inhibit ACAT in macrophages more strongly than ACAT in liver and are hence useful as prophylactic and therapeutic agents for arteriosclerosis, thus leading to completion of the present invention.

According to the present invention, there is thus provided a substituted vinylurea derivative represented by the following general formula (1):

wherein $R^1$ and $R^3$ are independently a phenyl group which may be substituted, $R^2$ is a phenyl group which may be substituted, or a cycloalkyl group, and wave lines mean that the bonding state may be either E or Z, with the proviso that the cases where $R^1$, $R^2$ and $R^3$ are unsubstituted phenyl groups, and where $R^1$ and $R^2$ are unsubstituted phenyl groups and $R^3$ is a 4-ethoxyphenyl group are excluded, or a salt thereof (hereinafter referred to as "the compound (1)").

According to the present invention, there is also provided a medicine comprising the compound (1) as an active ingredient.

According to the present invention, there is further provided a medicinal composition comprising the compound (1) and a pharmaceutically acceptable carrier.

According to the present invention, there is still further provided use of the compound (1) for a medicine.

According to the present invention, there is yet still further provided a method of preventing and treating arteriosclerosis, which comprises administering an effective amount of the compound (1) to a patient.

DETAILED DESCRIPTION OF THE PREFERRED EMBODIMENTS

The compounds (1) according to the present invention are represented by the general formula (1). Examples of substituents of the phenyl groups, which are represented by $R^1$, $R^2$ and $R^3$ in the formula (1) and may be substituted, include halogen atoms such as fluorine, chlorine and bromine atoms; halogenated $C_{1-6}$ alkyl groups such as fluoromethyl, chloromethyl and 1,1,1-trifluoromethyl groups; $C_{1-6}$ alkoxyl groups such as methoxy and ethoxy groups; an amino group; mono-$C_{1-6}$-alkylamino groups such as monomethylamino and monoethylamino groups; di-$C_{1-6}$-alkylamino groups such as dimethylamino and diethylamino groups; a hydroxyl group; C$_{7-16}$ aralkyloxy groups such as a benzyloxy group; a methylenedioxy group; a cyano group; a benzoyl group; C$_{2-7}$ alkanoyl groups such as acetyl and propionyl groups; a carbamoyl group; a carboxyl group; C$_{1-6}$ alkoxy-carbonyl groups such as methoxycarbonyl and ethoxycarbonyl groups; C$_{1-6}$ alkoxymethoxy groups such as methoxymethoxy group; C$_{2-7}$ alkanoyloxy groups such as acetyloxy and propionyloxy groups; a nitro group; a sulfonic group; a sulfonamide group; a thiol group; C$_{1-6}$ alkylthio groups such as methylthio and ethylthio groups; C$_{1-6}$ alkylsulfinyl groups such as methylsulfinyl and ethylsulfinyl groups; C$_{1-6}$ alkylsulfonyl groups such as mehylsulfonyl and ethylsulfonyl groups; C$_{1-6}$ alkyl groups such as methyl, ethyl, n-propyl and isopropyl groups; C$_{2-7}$ alkanoylamino groups such as acetylamino and propionylamino groups; a benzoylamino group; hydroxy-C$_{1-6}$-alkyl groups such as hydroxymethyl and hydroxyethyl groups; carboxy-C$_{1-6}$-alkyl groups such as carboxymethyl and carboxyethyl groups; C$_{2-6}$ alkenyl groups such as vinyl and allyl groups; C$_{2-7}$ alkanoyl-piperazinyl groups such as acetylpiperazinyl, propionylpiperazinyl, n-butyrylpiperazinyl and i-butyryl-piperazinyl groups; C$_{1-6}$ alkyl-aminocarbonylpiperazinyl groups such as methylaminocarbonylpiperazinyl, ethylaminocarbonylpiperazinyl, n-propylaminocarbonylpiperazinyl and i-propylaminocarbonylpiperazinyl groups; C$_{2-7}$ alkanoyl-aminomethyl groups such as acetylaminomethyl, propionylaminomethyl, n-butyrylaminomethyl and hexanoylaminomethyl groups; C$_{1-6}$-alkyl-aminocarbonyl-C$_{1-6}$-alkyl groups such as methylaminocarbonylmethyl, ethylaminocarbonylmethyl, methylaminocarbonylethyl, ethylaminocarbonylethyl, i-propylaminocarbonylmethyl and i-propylaminocarbonylethyl groups; C$_{1-6}$ alkyl-ureidomethyl groups such as methylureidomethyl, ethylureidomethyl, n-propylureidomethyl and i-propylureidomethyl groups; and N-C$_{1-6}$-alkoxy-carbonylpiperidinylcarbamoyl groups such as N-methoxycarbonyl-piperidinylcarbamoyl, N-ethoxycarbonyl-piperidinylcarbamoyl, N-n-propoxycarbonylpiperidinylcarbamoyl and N-i-propoxycarbonylpiperidinylcarbamoyl groups. One to three of these substituents may be substituted on the phenyl group.

Of these, 1–3 substituents selected from the group consisting of the halogen atoms, C$_{1-6}$ alkyl groups, C$_{1-6}$ alkoxyl groups, nitro group, hydroxyl group, methylenedioxy group, mono-C$_{1-6}$-alkylamino groups, di-C$_{1-6}$-alkylamino groups, amino group and carboxyl group are preferred, with 1–3 substituents selected from the group consisting of the fluorine atom, and methyl, isopropyl, methoxy, methylenedioxy, hydroxyl and dimethylamino groups being particularly preferred.

The above groups such as alkyl, alkoxy and alkanoyl include both linear and branched chains.

Examples of the cycloalkyl group represented by R$^2$ include C$_{3-7}$ cycloalkyl groups such as cyclopropyl, cyclobutyl, cyclopentyl and cyclohexyl groups, with C$_{5-7}$ cycloalkyl groups such as cyclopentyl and cyclohexyl groups being preferred.

In the present invention, any substituted vinylurea derivatives in which R$^1$, R$^2$ and R$^3$ are unsubstituted phenyl groups, and in which R$^1$ and R$^2$ are unsubstituted phenyl groups and R$^3$ is a 4-ethoxyphenyl group are excluded.

The compounds (1) according to the present invention may form salts when one or more amino compounds, carboxylic acids, sulfonic acids and/or the like have been substituted thereon. In this case, no particular limitation is imposed on the salts so far as they are pharmaceutically acceptable salts. Specific examples thereof include organic acid salts such as fumarates, maleates, citrates and tartrates, and inorganic acid salts such as hydrochlorides, hydrobromides and sulfates in the case where one or more amino compounds have been substituted; and salts such as sodium salts, potassium salts and calcium salts in the case where one or more carboxylic acids or sulfonic acids have been substituted.

Since the compounds (1) are olefins, they may be formed as geometric isomers or mixtures thereof according to the kinds of the substituents when R$^1$ and R$^2$ are different from each other. All of these geometric isomers are included in the present invention. The substituted vinylurea derivatives (1) may be present in the form of solvates typified by hydrates.

The compounds (1) according to the present invention can be prepared in accordance with any of, for example, the following Preparation Process 1 to 4.

Preparation Process 1:

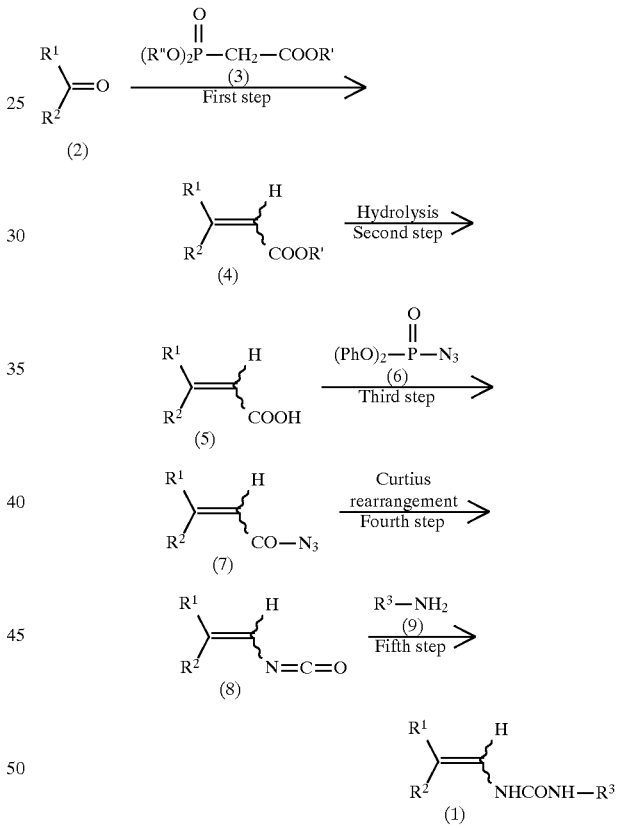

wherein R$^1$ to R$^3$ have the same meanings as defined above, R' and R" are lower alkyl groups, and Ph is a phenyl group.

As shown in the above reaction scheme, a ketone compound (2) is reacted with a compound (3) (a first step), the resultant compound (4) is then hydrolyzed into a carboxylic acid (5) (a second step). The carboxylic acid (5) is reacted with a compound (6) into an azide (7) (a third step), and the azide (7) is then subjected to Curtius rearrangement to obtain an isocyanate (8) (a fourth step). The isocyanate (8) is further reacted with an amine (9) (a fifth step), thereby obtaining a compound (1) according to the present invention.

The individual steps will hereinafter be described in detail.

The carbon-carbon double-bond reaction in the first step can also be conducted in accordance with the general Wittig reaction. However, the reaction can be more readily conducted when the Horner-Emons reaction developed from the Wittig reaction is used. Therefore, the phosphonate (3) is used as a reagent herein to conduct the Horner-Emons reaction.

The reaction in the first step is generally conducted in the presence of suitable base and solvent. Examples of the base used include sodium hydride, sodium methoxide, sodium ethoxide, potassium t-butoxide, sodium hydroxide and potassium hydroxide. No particular limitation is imposed on the solvent used so far as it does not affect the reaction. However, examples thereof include ethers such as tetrahydrofuran, dioxane and diethyl ether; amides such as dimethylformamide, dimethylacetamide and N-methyl-α-pyrrolidone; hydrocarbons such as benzene, toluene and xylene; alcohols such as ethanol, butanol, methoxyethanol and ethoxyethanol; and sulfoxides such as dimethyl sulfoxide.

The reaction is performed for 1 to 24 hours in a temperature range of from 0° C. to a temperature at which reflux occurs under heat. In the most preferred embodiment, the reaction is conducted at room temperature for 3–4 hours by adding an equimolar amount of the phosphonate (3) to the ketone compound (2) in anhydrous tetrahydrofuran and then adding an equimolar amount or a slightly excessive amount of sodium hydride.

The hydrolysis reaction in the second step is performed under ordinary conditions. More specifically, the reaction is conducted in a 1–10N aqueous solution of sodium hydroxide or potassium hydroxide. In some cases, an alcohol such as methanol or ethanol may be added according to the solubility of the compound (4). The reaction is conducted at a temperature of room temperature to 100° C. for 0.5 to 24 hours.

The azidation in the third step and the Curtius rearrangement in the fourth step are conducted by one-pot reaction without subjecting the reaction mixture to a post treatment on the way as it is.

The reactions in the third and fourth steps are generally conducted in the presence of suitable base and solvent. No particular limitation is imposed on the solvent used so far as it does not affect the reactions. However, examples thereof include hydrocarbons such as benzene, toluene and xylene.

Examples of the base used include triethylamine, pyrrolidine, piperidine and pyridine, with triethylamine being most preferred.

The reactions are performed for 0.5 to 8 hours in a temperature range of from room temperature to a temperature at which reflux occurs under heat. In the most preferred embodiment, the reactions are conducted for 1–3 hours under reflux by using an equimolar amount of the compound (6) to the carboxylic acid (5) in benzene and adding 1–2 equivalents of triethylamine.

The reaction in the fifth step is conducted as one pot reaction in the reaction mixture obtained in the third and fourth steps. The amino compound (9) used in the fifth step is preferably used in an amount of 1–2 equivalents to the carboxylic acid (5). The reaction is preferably performed at room temperature to 150° C. for 1–24 hours.

Preparation Process 2:

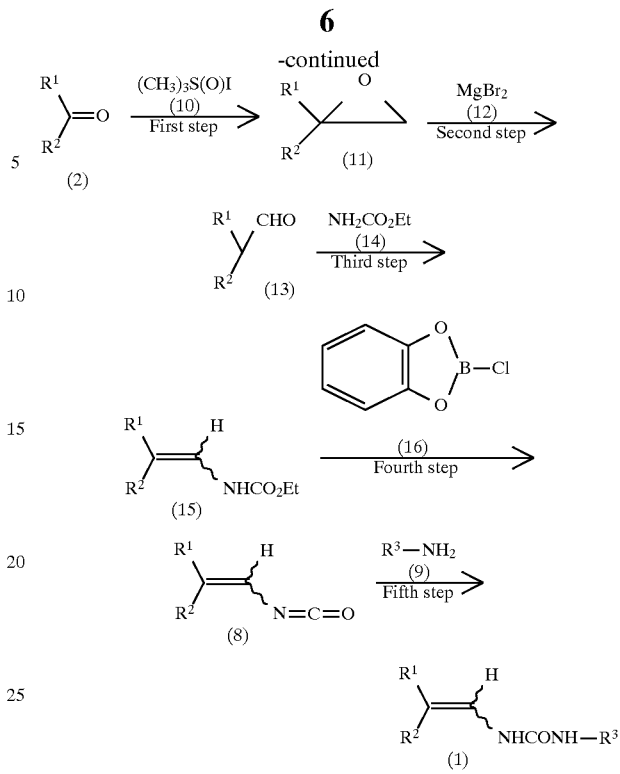

wherein $R^1$ to $R^3$ have the same meanings as defined above, and Et is an ethyl group.

As shown in the above reaction scheme, a ketone compound (2) is reacted with trimethylsulfoxonium iodide (10) into an epoxy compound (11) (a first step), and the epoxy ring is opened with magnesium bromide (12) into an aldehyde (13) (a second step). The compound (13) is condensed with ethyl carbamate (14) into an urethane (15), and the urethane (15) is then reacted with B-chloro-catechol borane (16) into an isocyanate (8) (a fourth step). The compound (8) is reacted with an amine (9) in the same manner as in the fifth step in the above-described Production Process 1, thereby obtaining a compound (1) according to the present invention.

The individual steps will hereinafter be described in detail.

The epoxidation reaction in the first step is conducted by using dimethyl sulfoxide as a solvent, adding sodium hydride in an amount of 1–1.5 equivalents to the ketone compound (2) at 0° C. to room temperature to form a dimsyl sodium of a base. To this reaction mixture, is added trimethylsulfoxonium iodide (10) in an amount of 1–1.2 equivalents to the ketone compound (2) to conduct a reaction at room temperature for 1–3 hours. A solution of the ketone compound (2) in dimethyl sulfoxide or tetrahydrofuran is then added dropwise over 15 minutes to 1 hour at 0° C. to room temperature, followed by a reaction at 0° C. to room temperature for 1–24 hours, thereby obtaining an epoxide (11) (this synthesis procedure follows the process described in "Experimental Chemical Course 21: Organic Synthesis III, Forth Edition (Maruzen), p. 101").

Incidentally, besides dimethyl sulfoxide and tetrahydrofuran, any solvent may be used as the solvent used in the addition of the ketone compound (2) without any particular limitation so far as it does not affect the reaction.

In the epoxy ring opening reaction in the second step, magnesium bromide (12) or a boron trifluoride ether salt is used as an acid catalyst. However, magnesium bromide (12) is preferred. As the solvent, besides the ethers, any solvent may be used without any particular limitation so far as it does not affect the reaction. The reaction is conducted by adding a ether solution of the epoxide (11) dropwise at −10° C. to room temperature in the presence of the acid catalyst in the ether and holding the reaction mixture at the same temperature for 5 minutes to 24 hours, thereby obtaining the aldehyde (13) (this reaction follows, for example, the process described in the above-mentioned "Experimental Chemical Course 21: Organic Synthesis III, Forth Edition (Maruzen), p. 101").

The dehydration condensation reaction of the aldehyde (13) with ethyl carbamate (14) in the third step is generally conducted in the presence of suitable acid catalyst and solvent. No particular limitation is imposed on the solvent used so far as it does not affect the reaction. However, examples thereof include hydrocarbons such as benzene, toluene and xylene. Examples of the acid catalyst used include p-toluene-sulfonic acid, methanesulfonic acid and sulfuric acid, with p-toluenesulfonic acid being preferred. The reaction is performed in a temperature range of from room temperature to a temperature at which reflux occurs under heat. When the reaction is carried out under reflux, the use of a Dean-Stark apparatus facilitates the progress of the reaction. The reaction is conducted for 0.5 to 8 hours. In the most preferred embodiment, the reaction is conducted by means of the Dean-Stark apparatus for 1–3 hours under reflux by using an equimolar amount of ethyl carbamate (14) to the aldehyde (13) in toluene and adding 0.05–0.1 equivalents of p-toluenesulfonic acid.

The reactions in the fourth and fifth steps are reactions in which the urethane (15) is reacted with B-chlorocatecohol borane (16) into the isocyanate (8), and this product is reacted with the amine (9) by one-pot reaction as it is, thereby obtaining the compound (1) according to the present invention. The reactions may be performed in accordance with the process described in "V. L. K. Valli and H. Alper, J. Org. Chem., 60, 257–258 (1995)". More specifically, a toluene solution containing B-chlorocatecohol borane (16) in an equimolar amount to the urethane (15) and triethylamine as a base in an amount of 1–2 equivalents to the urethane (15) are used, and toluene is used as a solvent to heat the mixture under reflux for 1–3 hours, thereby obtaining the isocyanate (8). After the reaction mixture is cooled, the amine (9) in an amount of 1–3 equivalents to the urethane (15) is added to conduct a reaction by one-pot reaction at room temperature to 150° C. for 1–24 hours as it is, thereby obtaining the compound (1) according to the present invention. At this time, besides toluene, hydrocarbons such as benzene and xylene are preferably used. In addition, any solvent may be used without any particular limitation so far as it does not affect the reaction. No particular limitation is also imposed on the base if a suitable base exists in addition to triethylamine.

Among the amines (9) used in the fifth steps in the above-described Preparation Processes 1 and 2, those not marketed can be prepared in accordance with, for example, the following reaction schemes:

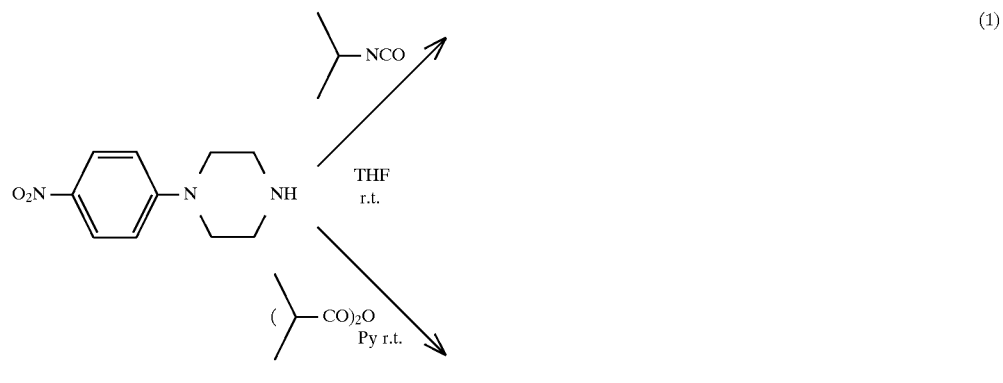

(1)

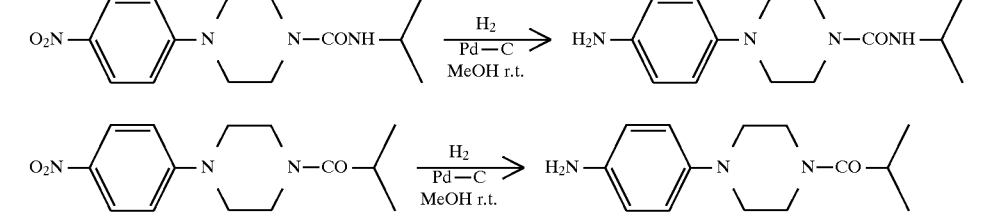

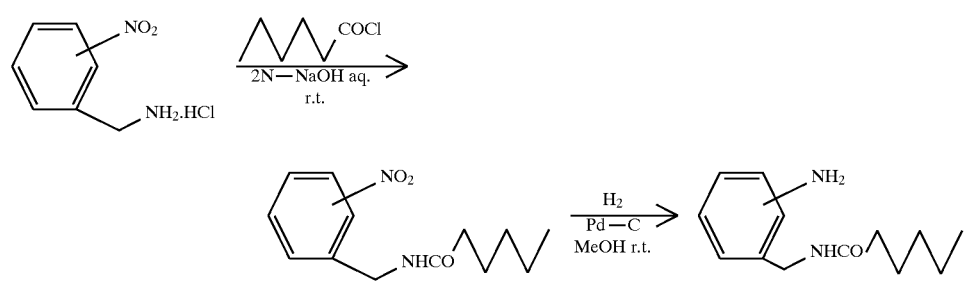

(2)

-continued
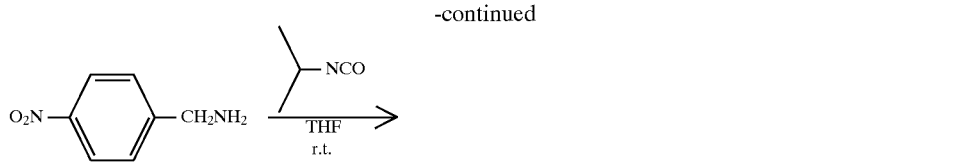
(3)
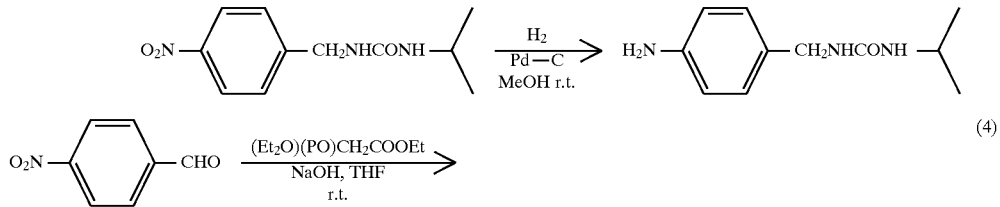
(4)
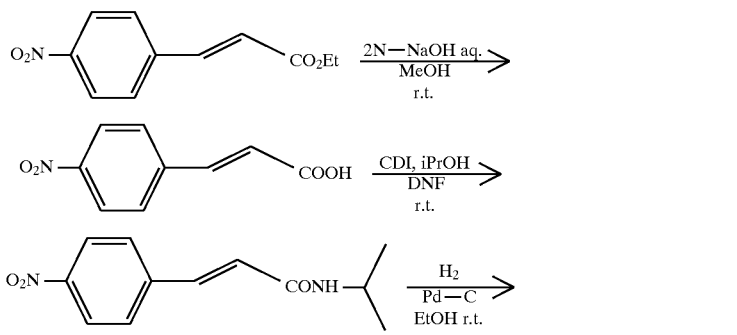
CDI: 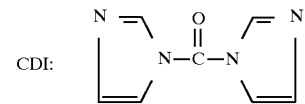
(5)
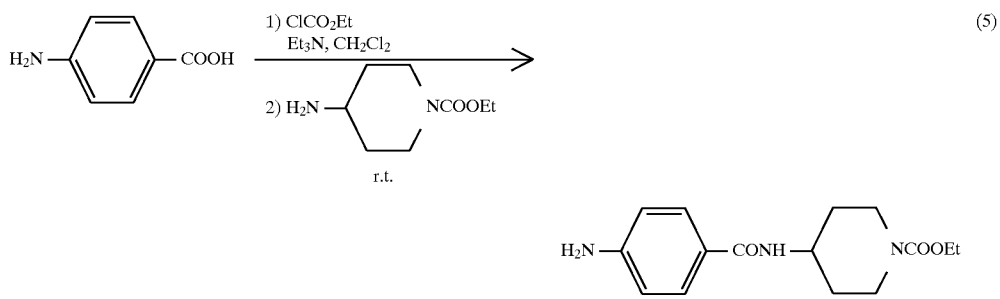
Preparation Process 3:
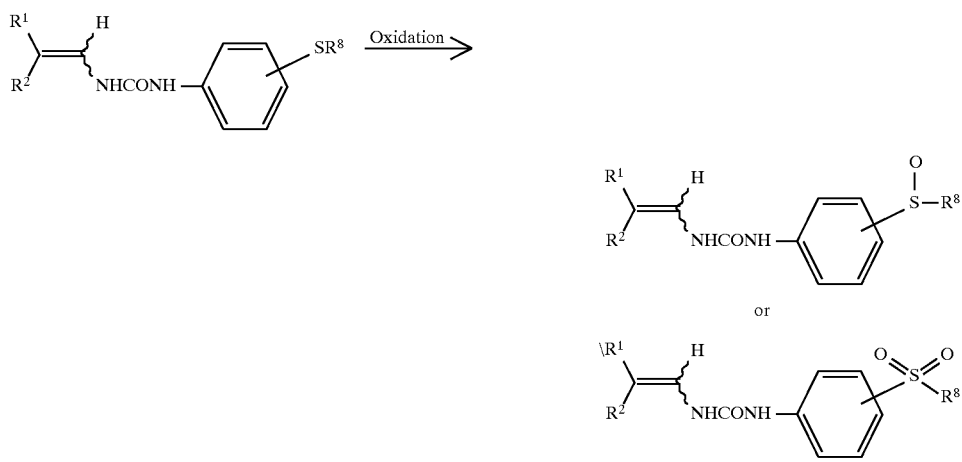

wherein $R^1$ and $R^2$ have the same meanings as defined above, and $R^8$ is a $C_{1-6}$ alkyl group.

In the case where a compound, in which $R^3$ is an alkylthiophenyl group, has been obtained in accordance with the above-described Preparation Process 1 or 2, such a compound can be oxidized in accordance with the above reaction scheme, thereby converting it into a compound in which $R^3$ is an alkylsulfinylphenyl or alkylsulfonylphenyl group. m-Chloroperbenzoic acid or aqueous hydrogen peroxide is generally used as an oxidizing agent used in this reaction. No particular limitation is imposed on the solvent used so far as it does not affect the reaction. However, for example, a halogenated hydrocarbon such as methylene chloride or chloroform is preferably used where the oxidizing agent is m-chloroperbenzoic acid, and an alcohol such as methanol or ethanol, or acetic acid is preferably used where the oxidizing agent is aqueous hydrogen peroxide. The reaction is conducted in a temperature range of from 0° C. to a temperature at which reflux occurs under heat. It is preferable to perform the reaction for about 1–24 hours.

Preparation Process 4:

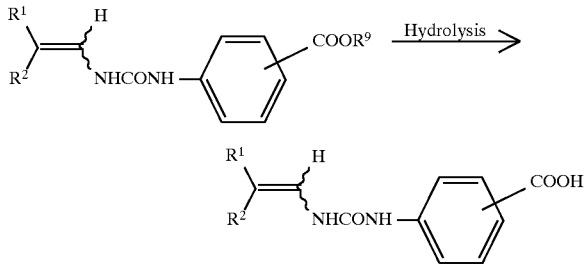

wherein $R^1$ and $R^2$ have the same meanings as defined above, and $R^9$ is a $C_{1-6}$ alkyl group.

In the case where a compound, in which $R^3$ is an alkoxycarbonylphenyl group, has been obtained in accordance with the above-described Preparation Process 1 or 2, such a compound can be hydrolyzed in accordance with the above reaction scheme, thereby converting it into a compound in which $R^3$ is a carboxyl group. This hydrolysis reaction can be conducted under ordinary conditions. More specifically, it is only necessary to conduct the reaction in a 1–10N aqueous solution of sodium hydroxide or potassium hydroxide. An alcohol such as methanol or ethanol may be added according to the kind of the starting material. The reaction is preferably conducted at a temperature of room temperature to 100° C. for 0.5 to 24 hours.

The isolation and purification of the intended compound (1) in each of the above reaction schemes can be performed in a method known per se in the art, for example, washing, extraction, recrystallization and/or chromatography. The compound (1) may also be converted into a salt in a method known per se in the art.

The thus-obtained compounds (1) according to the present invention are useful in preventing and treating arteriosclerosis, and various diseases related thereto, for example, cerebral infarction, transient ischemic attack, angina pectoris, peripheral thrombus and peripheral occlusion.

When the compound (1) according to the present invention is used as such a medicine, it is only necessary to mix the compound (1) with a solid or liquid carrier known in this technical field to prepare a medicinal composition (medicinal preparation) suitable for parenteral administration, oral administration or external administration. Examples of the medicinal preparation include liquid preparations such as injections, inhalants, syrups and emulsions, solid preparations such as tablets, capsules and granules, and external preparations such as ointments and suppositories. These preparations may contain additives usually used, such as auxiliaries, stabilizers, wetting agents, emulsifiers, absorbefacients and surfactants, as needed. Specific examples of the additives include distilled water for injection, Ringer's solution, glucose, sucrose syrup, gelatin, edible oil, cacao butter, magnesium stearate and talc.

When the compound (1) according to the present invention is used as a prophylactic and therapeutic agent for arteriosclerosis, the dose thereof varies according to the administration method thereof, and the age, weight and diseased condition of a patient to be dosed. However, it is preferable to use the compound (1) in a dose of 0.1–1,000 mg per day for an adult in the case of oral administration.

The present invention will hereinafter be described more specifically by the following Examples and Test Example. However, the present invention is not limited to these examples.

EXAMPLE 1

Added to a mixture of 1.00 g of 3,3-di(3-nitro-phenyl) propenic acid, 0.88 g of diphenylphosphoryl azide and 10 ml of benzene were 0.34 g of triethylamine, followed by refluxing for 1 hour. After cooling, 0.41 g of difluoroaniline were added, and the resultant mixture was stirred for 12 hours at room temperature. Water was then added to the reaction mixture, and extraction was conducted with ethyl acetate. The extract was washed with water, 1N HCl and saturated saline in that order. After the resultant organic layer was dried over anhydrous sodium sulfate, the solvent was distilled off, and the residue was subjected to column chromatography on silica gel. A chloroform-eluted fraction was concentrated under reduced pressure, thereby obtaining 1.05 g (yield: 75.0%) of the intended 1-[2,2-di-(3-nitrophenyl)]vinyl-3-(2,4-difluorophenyl)urea (Compound 1) as yellow noncrystalline powder. The data of Compound 1 are shown in Table 1.

EXAMPLE 2

Added to a solution of 1.00 g of ethyl N-[2,2-di-(2-methylphenyl)]vinyl-carbamate and 0.34 g of triethylamine in toluene (10 ml) were 7 ml of a toluene solution of 0.5 mol/liter of B-chlorocatecohol borane, followed by refluxing and stirring for 1 hour. After cooling, 0.44 g of 2,4-difluoroaniline were added, and the resultant mixture was stirred for 12 hours at room temperature. Water was then added to the reaction mixture, and extraction was conducted with ethyl acetate. The extract was washed with water, 1N HCl and saturated saline in that order. After the resultant organic layer was dried over anhydrous sodium sulfate, the solvent was distilled off, and the residue was subjected to column chromatography on silica gel. A chloroform-eluted fraction was concentrated under reduced pressure, thereby obtaining 495 mg (yield: 38.4%) of the intended 1-[2,2-di-(2-methylphenyl)]vinyl-3-(2,4-difluorophenyl)urea (Compound 2) as colorless crystals. The data of Compound 2 are shown in Table 1.

EXAMPLES 3–18

Compounds 3–18 were prepared in the same manner as in Example 1 or 2. The data of Compounds 3–18 are shown in Tables 1 to 4.

TABLE 1

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 1 | 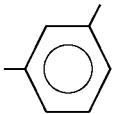 | 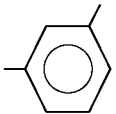 | 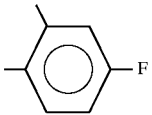 | — | Yellow non-crystalline powder | 441 | 6.60–8.20(m, 12H) |
| 2 | 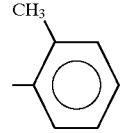 | 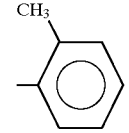 | 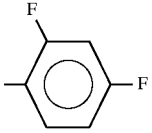 | — | Colorless crystals (213–214) | 379 | 2.12(s, 3H), 2.20(s, 3H), 6.60–7.50(m, 10H), 7.90–8.80 (m, 3H) |
| 3 | 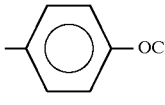 | 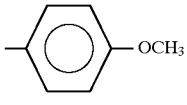 | 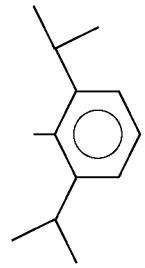 | — | Colorless cyrstals (169–171) | 459 | 1.05(d, 6H), 1.12(d, 6H), 3.15(q, 2H), 3.76(s, 3H). 3.77(s, 3H), 6.19(br, 1H), 6.61 (br, 1H), 6.74–7.29(m, 12H) |
| 4 |  | 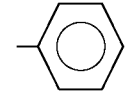 | 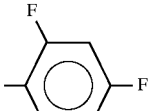 | — | Colorless crystals (209–210) | 351 | 6.30–8.20(m, 14H) |
| 5 | 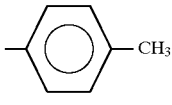 | 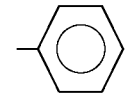 | 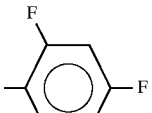 | E. Z | Colorless crystals | 364 | 1.56(s, 3H), 6.40–8.05(m, 13H) |
| 6 | 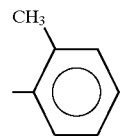 | 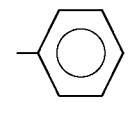 | 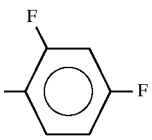 | E. Z | Colorless crystals | 364 | 2.15(s. 3H), 6.65–7.05(m, 3H), 7.05–7.70(m, 9H). 8.00–8.40(m, 1H) |

TABLE 2

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 7 | 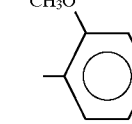 | 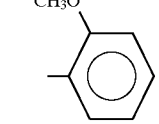 | 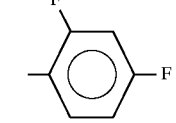 | — | Colorless crystals (208–210) | 410 | 3.68(s,3H), 3.80(s, 3H), 6.60–8.40(m, 12H) |
| 8 |  | 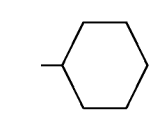 | 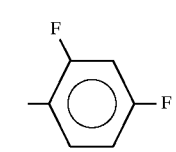 | E. Z | Colorless crystals | 371 | 1.00–1.35(m, 5H), 1.63(d, 1H), 1.74(m, 4H), 2.16(l, 1H), 2.34(s, 3H), 6.28(d, 1H). 6.36(br, 1H), 6.64 (d, 1H). 6.79(m, 2H), 7.02(d, 2H), 7.17 (d, 2H), 7.82 (m, 1H) |

TABLE 2-continued

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 9 | 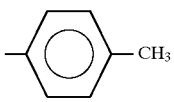 | 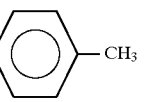 | 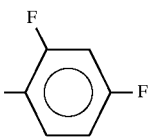 | — | Colorless crystals (219–220) | 379 | 2.29(s, 3H), 2.38(s, 3H). 6.60–7.70(m, 13H) |
| 10 | 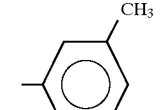 | 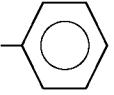 | 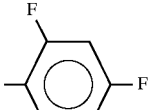 | E. Z | Colorless crystals | 365 | 2.28(s, 3H), 2.32(s, 3H), 6.60–8.26(m, 14H) |
| 11 | 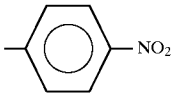 |  | 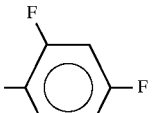 | E. Z | Pale yellow crystals | 396 | 6.60–8.30(m, 13H) |

TABLE 3

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 12 | 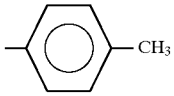 | 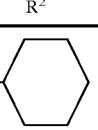 | 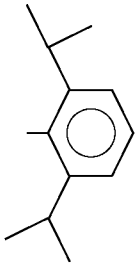 | E. Z | Colorless crystals | 419 | 0.80–1.35(m, 17H), 1.60(d, 1H), 1.71(m, 4H), 2.10(t, 1H), 2.23(s, 3H), 3.09(m, 2H), 5.62(s, 1H), 5.70(d, 1H). 6.59(d, 1H), 6.62(m, 2H), 6.82(d, 2H), 7.00(d, 2H), 7.20(t, 1H) |
| 13 | 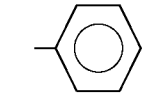 |  | 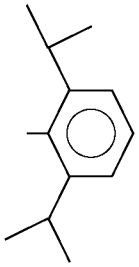 | — | Colorless crystals (219–220) | 398 | 0.80–1.40(m, 12H), 2.90–3.40(m, 2H), 6.00–7.80(m, 14H) |
| 14 |  | 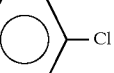 | 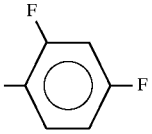 | — | Colorless crystals (201–203) | 418 | 6.60–7.60(m, 12H) |
| 15 | 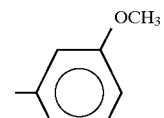 |  | 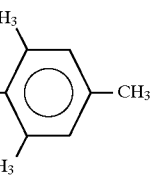 | — | Colorless crystals (155–157) | 417 | 2.11(s, 6H), 2.23(s, 3H), 3.65(s, 3H), 3.70(s, 3H), 6.30–7.50(m, 2H) |

TABLE 4

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 16 | –⟨phenyl⟩–OCH₃ | –⟨phenyl⟩–OCH₃ | –⟨phenyl⟩(F,F) | — | Colorless crystals (159–161) | 411 | 3.79(s, 6H), 6.77–7.25(m, 14H) |
| 17 | –⟨phenyl⟩(OCH₃) | –⟨phenyl⟩(OCH₃) | –⟨phenyl⟩–F | — | Colorless crystals (168–170) | 411 | 3.76(s, 6H), 6.60–8.20(m, 12H) |
| 18 | –⟨phenyl⟩ | –⟨phenyl⟩ | –⟨phenyl⟩–COOCH₃ | — | Colorless crystals (177–178) | 373 | 3.85(s, 3H), 6.80–7.50(m, 13H), 7.70–8.10(m, 2H) |

EXAMPLE 19

Synthesis of 1-(2,2-diphenyl)vinyl-3-(4-carboxy-phenyl)urea (Compound 19):

Dissolved in methanol were 50 mg of 1-(2,2-diphenyl)vinyl-3-(4-methoxycarbonylphenyl)urea (Compound 18) obtained in Example 18. To the solution were added 2 ml of a 2N aqueous solution of sodium hydroxide. The resultant mixture was heated at 60° C. for 3 hours. After the reaction mixture was then concentrated under reduced pressure, the concentrate was acidified with 1N hydrochloric acid and extracted with ethyl acetate. The resultant organic layer was washed with water and saturated saline in that order, dried over anhydrous sodium sulfate and then concentrated under reduced pressure, thereby obtaining 45 mg (yield: 96%) of the intended Compound 19 as crystals. The data are shown in Table 5.

EXAMPLES 20 AND 21

Compounds 20 and 21 were obtained in the same manner as in Example 1 or 2. The data are shown in Table 5.

EXAMPLE 22

Compound 22 was obtained in the same manner as in Example 19. The data are shown in Table 5.

EXAMPLES 23–26

Compounds 23–26 were obtained in the same manner as in Example 1 or 2. The data are shown in Tables 5 and 6.

EXAMPLE 27

Synthesis of 1-(2,2-diphenyl)vinyl-3-(3-methyl-sulfinylphenyl)urea (Compound 27):

Dissolved in 20 ml of dichloromethane were 500 mg (1.39 mmol) of 1-(2,2-diphenyl)vinyl-3-(3-methylthio-phenyl)urea (Compound 26) obtained in Example 26. To the solution were added 240 mg (1.39 mmol) of m-chloroperbenzoic acid. The resultant mixture was stirred for 3 hours at room temperature. After the reaction mixture was then washed with a saturated solution of sodium hydrogencarbonate and water in that order, the resultant organic layer was dried over anhydrous sodium sulfate. After dichloromethane was distilled off, the residue was crystallized with ether, thereby obtaining 225 mg (yield: 43.1%) of the intended Compound 27 as colorless crystals. The data are shown in Table 6.

EXAMPLE 28

Synthesis of 1-(2,2-diphenyl)vinyl-3-(3-methyl-sulfonylphenyl)urea (Compound 28):

Dissolved in 20 ml of dichloromethane were 500 mg (1.39 mmol) of 1-(2,2-diphenyl)vinyl-3-(3-methylthio-phenyl)urea (Compound 26) obtained in Example 26. To the solution were added 600 mg (3.48 mmol) of m-chloroperbenzoic acid. The resultant mixture was stirred for 12 hours at room temperature. After the reaction mixture was then washed with a saturated solution of sodium hydrogencarbonate and water in that order, the resultant organic layer was dried over anhydrous sodium sulfate. After dichloromethane was distilled off, the residue was subjected to column chromatography on silica gel. A 1% MeOH-CHCl₃-eluted fraction was concentrated under reduced pressure, thereby obtaining 78 mg (yield: 14.3%) of the intended Compound 28 as crystals. The data are shown in Table 6.

EXAMPLES 29–55

Compounds 29–55 were obtained in the same manner as in Example 1 or 2. The data are shown in Tables 6 to 14.

TABLE 5

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 19 | phenyl | phenyl | C₆H₄-COOH | — | Colorless crystals (286–287) | 359 | 6.90–8.10(m, 15H) |
| 20 | phenyl | phenyl | C₆H₄-N(CH₃)₂ | — | Pale yellow crystals (205–206) | 358 | 1.20(t, 3H), 2.93(s, 6H), 3.48 (q, 2H), 6.33(br, 1H), 6.57 (dd, 2H), 6.76(d, 1H), 6.98(d, 2H), 7.12–7.30(m, 10H), 7.38(d, 1H) |
| 21 | phenyl | phenyl | C₆H₄-COOCH₃ | — | Colorless crystals (180–181) | 373 | 3.81(s, 3H), 6.85–7.63(m, 10H), 7.91 (dd, 1H), 8.50(d, 1H), 10.32(s, 1H) |
| 22 | phenyl | phenyl | C₆H₄-COOH | — | Colorless crystals (258–259) | | 6.67(s, 1H), 7.06–7.41(m, 10H), 7.61(ddd, 1H), 7.83(dd, 1H), 11.28(s, 1H) |
| 23 | phenyl | phenyl | C₆H₂(OCH₃)₂(COCH₃) | — | Colorless crystals (168–169) | 417 | 2.56(s, 3H), 3.89(s, 3H), 3.99(s, 3H), 6.60–7.70(m, 12H), 8.34(s, 1H) |
| 24 | phenyl | phenyl | C₆H₃Cl₂ | — | Colorless crystals (226–227) | 383 | 6.80–7.60(m, 14H) |

TABLE 6

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 25 | phenyl | phenyl | methylenedioxyphenyl | — | Colorless crystals (228–229) | 359 | 5.91(s, 2H), 6.64(d, 1H), 6.68(d, 1H), 7.02(d,1H), 7.15–7.46(m, 13H) |
| 26 | phenyl | phenyl | C₆H₄-SCH₃ | — | Colorless crystals (187–188) | 361 | 2.44(s, 3H), 6.88(d, 1H), 7.04(d, 1H), 7.12–7.45(m, 15H) |

TABLE 6-continued

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 27 | phenyl | phenyl | 3-(S(=O)CH₃)phenyl | — | Colorless crystals (300>) | 377 | 3.95(s, 3H), 7.17–7.49(m, 15H), 7.59(t, 1H), 7.67(d, 1H) |
| 28 | phenyl | phenyl | 3-(SO₂CH₃)phenyl | — | Colorless crystals (230–232) | 393 | 2.86(s, 3H), 7.18–7.67(d, 16H) |
| 29 | 4-(OCH₂OCH₃)phenyl | 4-(OCH₂OCH₃)phenyl | 2,4-difluorophenyl | — | Colorless crystals (171) | 471 | 3.47(s, 3H), 3.50(s, 3H), 5.15 (s, 2H), 5.19(s, 2H), 6.70–7.40 (m, 11H), 7.80–8.20(m,H) |

TABLE 7

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 30 | 4-hydroxyphenyl | 4-hydroxyphenyl | 2,4-difluorophenyl | — | Colorless crystals (230–232) | 383 | 6.60–8.30(m, 12H) |
| 31 | 4-fluorophenyl | 4-fluorophenyl | 2,4-difluorophenyl | — | Colorless crystals (202–203) | 387 | 6.75–7.29(m, 12H), 7.68(d, 1H), 7.97–8.03(m, 1H) |
| 32 | 4-fluorophenyl | 4-fluorophenyl | 2,6-diisopropylphenyl | — | Colorless crystals (248–250) | 435 | 1.09(dd, 2H), 3.11 (m, 2H), 6.07(d,1H), 0.78–7.33(m, 14H) |
| 33 | 3,4-methylenedioxyphenyl | 3,4-methylenedioxyphenyl | 2,4-difluorophenyl | — | Colorless crystals (191–192) | 439 | 5.93(s, 1H), 5.98(s, 1H), 6.07(s, 4H), 6.65–6.73(m, 3H), 6.83–6.87(m, 3H), 7.30(d, 2H), 7.34(dd, 2H) |

TABLE 8

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 34 | (3-methyl-4-aminophenyl, NH₂) | (3-methyl-4-aminophenyl, NH₂) | (2,4-difluorophenyl, F, F) | — | Yellow non-crystalline powder | 331 | 6.40–7.50(m, 11H), 7.60–8.40(m, 1H) |
| 35 | (3,4-dimethoxyphenyl, OCH₃, OCH₃) | (3,4-dimethoxyphenyl, OCH₃, OCH₃) | (2,6-diisopropylphenyl) | — | Colorless non-crystalline powder | 519 | 1.09(d, 12H) 3.00–3.40(m, 2H), 3.80–4.00(br, s, 12H), 6.20–7.50(m, 12H) |
| 36 | (3,4-dimethoxyphenyl, OCH₃, OCH₃) | (3,4-dimethoxyphenyl, OCH₃, OCH₃) | (2,4-difluorophenyl, F, F) | — | Colorless crystals (218–222) | 471 | 3.68(s, 3H), 3.71(s, 3H), 3.85(s, 6H), 6.60–7.00(m, 8H), 7.20–8.40(m, 4H) |

TABLE 9

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 37 | (4-pentyloxyphenyl, O(CH₂)₄CH₃) | (4-pentyloxyphenyl, O(CH₂)₄CH₃) | (2,6-diisopropylphenyl) | — | Colorless waxy substance | 571 | 0.80–2.00(m, 30H), 3.00–3.40(m, 2H), 3.88(t, 4H), 6.00–6.30(br, 1H), 6.50–7.40(m, 13H) |
| 38 | (benzo[1,3]dioxol-5-yl) | (benzo[1,3]dioxol-5-yl) | (2,6-diisopropylphenyl) | — | Colorless crystals (183–185) | 487 | 1.13(s, 12H), 3.06(m, 2H), 5.96 (s, 2H), 6.07 (s, 2H), 6.55(m, 1H), 6.64–6.83(m, 4H), 6.95–7.16(m, 2H), 7.12(d, 2H), 7.22(t, 1H), 8.00 (br, 2H) |
| 39 | (phenyl) | (phenyl) | (4-(4-isobutyrylpiperazin-1-yl)phenyl, N N—CO—) | — | Colorless crystals (220–230) | 469 | 1.15(d, 6H), 2.84(m,1H), 2.80–3.30(m, 4H), 3.50–3.90(m, 4H), 6.84(d, 2H), 7.00–7.60(m, 13H) |

TABLE 10

| Compound No. | R¹ | R² | R³ | Geom. isomer | m.p. (°C.) | MS FAB. Pos. | ¹H-NMR data (CDCl₃,J) |
|---|---|---|---|---|---|---|---|
| 40 | 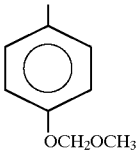 | 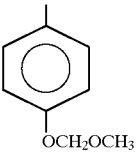 | 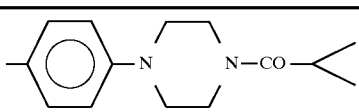 | — | Colorless non-crystalline powder | 589 | 1.10(s, 3H), 1.17(s, 3H), 2.64–3.20 (m, 5H), 3.46(s, 6H), 3.62–3.68 (m, 4H), 5.12(d, 4H), 6.75–7.19 (m, 15H) |
| 41 |  | 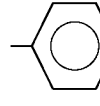 | 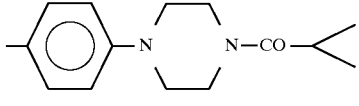 | — | Colorless oily substance | 529 | 1.14(d, 6H), 2.83(m, 1H), 2.80–3.30(m, 4H), 3.50–4.00 (m, 4H), 3.75(s, 3H), 3.77(s, 3H), 6.50–7.40(m, 13H) |
| 42 | 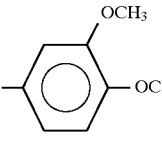 | 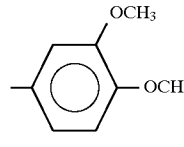 | 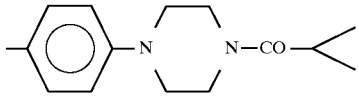 | — | Colorless non-crystalline powder | 589 | 1.14(d, 6H), 2.60–3.00 (m, 1H), 3.00–3.20(m, 4H), 3.60–4.00 (m, 4H), 3.71(s, 3H), 3.75(s, 3H), 3.84(s, 6H), 6.60–7.00 (m, 8H), 7.20–7.80(m, 5H) |

TABLE 11

| Compound No. | R¹ | R² | R³ | Geom. isomer | m.p. (°C.) | MS FAB. Pos. | ¹H-NMR data (CDCl₃,J) |
|---|---|---|---|---|---|---|---|
| 43 | 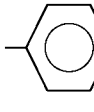 | 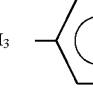 | 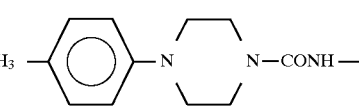 | — | Colorless crystals (201–202) | 544 | 1.17(d, 6H), 2.90–3.35(m, 4H), 3.40–3.70(m, 4H), 3.76(s, 3H), 3.77(s, 3H), 3.99(m, 1H), 6.70–7.50(m, 15H) |
| 44 |  | 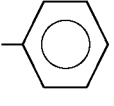 | 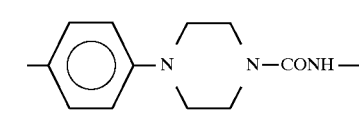 | — | Colorless crystals (241) | 484 | 1.17(d, 6H), 2.90–3.30(m, 4H), 3.30–3.70(m, 4H), 3.80–4.10(m, 1H), 6.84(d, 2H), 7.00–7.60(m, 13H) |

TABLE 11-continued

| Compound No. | R¹ | R² | R³ | Geom. isomer | m.p. (°C.) | MS FAB. Pos. | ¹H-NMR data (CDCl₃,J) |
|---|---|---|---|---|---|---|---|
| 45 | ⌬—OCH₃ | ⌬—OCH₃ | ⌬—CH₂NHCO(CH₂)₄CH₃ | — | Colorless crystals (182–184) | 502 | 9.88(t, 3H), 1.26–1.57(m, 6H), 2.08–2.23(m, 2H), 3.79(s, 3H), 3.83(s, 3H), 4.22–4.28(m, 2H), 6.74–7.38(m, 15H), 8.37(br, 1H) |
| 46 | ⌬—OCH₃ | ⌬—OCH₃ | ⌬—CH₂NHCO(CH₂)₄CH₃ | — | Colorless crystals (211–212) | 502 | 0.87(t, 3H), 1.26–1.64(m, 6H), 2.07–2.22(m, 2H), 3.79(s, 3H), 3.83(s, 3H), 4.26(br, 2H), 6.74–7.31 (m, 14H) |

TABLE 12

| Compound No. | R¹ | R² | R³ | Geom. isomer | m.p. (°C.) | MS FAB. Pos. | ¹H-NMR data (CDCl₃,J) |
|---|---|---|---|---|---|---|---|
| 47 | ⌬—OCH₂OCH₃ | ⌬—OCH₂OCH₃ | ⌬—CH₂NHCO(CH₂)₄CH₃ | — | Colorless non-crystalline powder | 562 | 0.86(t, 3H), 1.23–1.29(m, 4H), 3.47(s, 3H), 3.50(s, 3H), 1.55(quint., 2H), 2.08(t, 2H), 4.23(d, 2H), 5.15(s, 2H), 5.18(s, 2H), 6.00(t, 1H), 6.60(br, 1H), 6.86–7.29(m, 13H), 7.60(br, 1H) |
| 48 | methylenedioxyphenyl | methylenedioxyphenyl | ⌬—CH₂NHCO(CH₂)₄CH₃ | — | Colorless crystals (192–193) | 530 | 0.87(t, 3H), 1.24–1.33(m, 4H), 1.54–1.58(m, 2H), 2.12(t, 2H), 4.21 (d, 2H), 5.92(s, 2H), 5.95(s, 2H), 6.07(t, 1H), 6.62–6.71 (m, 5H), 6.81–6.86(m, 2H), 6.93(br, 1H), 7.13–7.23(m, 4H), 7.58(br, 1H) |
| 49 | ⌬—O(CH₂)₄CH₃ | ⌬—O(CH₂)₄CH₃ | ⌬—CH₂NHCO(CH₂)₄CH₃ | — | Colorless crystals (190–191) | 614 | 0.84–0.97(m, 9H) 1.23–1.58(m, 14H), 1.78(m, 4H), 2.08(t, 2H), 3.00–3.96(m, 4H), 4.21 (d, 2H), 5.91 (t, 1H), 0.78(d, 2H), 6.84–6.93(m, 4H), 7.09–7.29(m, 8H), 7.46(br, 1H) |

TABLE 13

| Compound No. | R¹ | R² | R³ | Geom. isomer | m.p. (°C.) | FAB. Pos. | ¹H-NMR data (CDCl₃.J) |
|---|---|---|---|---|---|---|---|
| 50 | 4-O(CH₂)₄CH₃-C₆H₄- | 4-O(CH₂)₄CH₃-C₆H₄- | 4-(CH₂NHCO(CH₂)₄CH₃)-C₆H₄- | — | Colorless crystals (158–159) | 614 | 0.82–0.96(m, 9H), 1.19–2.14(m, 18H), 3.90(q, 4H), 3.92(m, 1H), 4.13(d, 2H), 4.25(m 1H), 6.56(br, 1H), 6.75–6.95(m, 7H), 7.03–7.21(m, 6H), 7.70(d, 1H), 8.15(s, 1H) |
| 51 | 4-OCH₃-C₆H₄- | 4-OCH₃-C₆H₄- | 4-((CH₂)₂CONH-cyclopropyl)-C₆H₄- | — | Colorless crystals (246–248) | 488 | 1.00(s, 3H), 1.01(s, 3H), 2.27(t, 2H), 2.72(t, 2H), 3.73 (s,3H), 3.82(s, 3H), 3.78–3.84(m,1H), 6.84(d, 2H), 7.02–7.16(m, 9H), 7.27(d, 2H), 7.55(d, 1H), 7.83(d, 1H), 8.91 (s, 1H) |
| 52 | 3,4-methylenedioxyphenyl | 3,4-methylenedioxyphenyl | 4-((CH₂)₂CONH-cyclopropyl)-C₆H₄- | — | Colorless crystals (240, decomposed) | 516 | 1.00(s, 3H), 1.02(s, 3H), 2.27(t, 2H), 2.72(t, 2H), 3.81 (m, 1H), 5.97(s, 2H), 6.07(s, 2H), 6.54–7.28(m, 9H), 7.54 (d, 1H) |

TABLE 14

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 53 | 4-OCH₃-C₆H₄- | 4-OCH₃-C₆H₄- | 4-(piperazinyl-N-CONH-cyclopropyl)-C₆H₄- | — | Colorless crystals (235–237) | 489 | 1.03(d, 6H), 3.68(m, 1H), 3.73(s, 3H), 3.82(m, 1H), 4.11 (d, 2H), 5.65(d, 1H), 6.02(dd, 1H), 6.84 (dd, 2H), 7.02–7.06(m, 4H), 7.11–7.16(m, 3H), 7.31 (d, 2H), 7.84(d, 1H), 8.96(s, 1H) |

TABLE 14-continued

| Compound No. | R¹ | R² | R³ | Geom. isomer | m.p. (°C.) | MS FAB. Pos. | ¹H-NMR data (CDCl₃.J) |
|---|---|---|---|---|---|---|---|
| 54 | ![4-OCH2OCH3-phenyl] | ![4-OCH2OCH3-phenyl] | ![4-(CH2NHCONH-iPr)-phenyl] | — | Colorless crystals (219–220) | 549 | 1.03(d, 6H), 3.37(s, 3H), 3.43(s, 3H), 3.68(m, 1H), 4.00(d, 2H), 5.14(s, 2H), 5.24(s, 2H), 5.65(br, 1H), 6.02(br, 1H), 6.92(dd, 2H), 7.03(dd, 2H), 7.11–7.17(m, 7H), 7.31(d, 2H), 7.90(d, 1H), 8.98(s, 1H) |
| 55 | ![4-OCH3-phenyl] | ![4-OCH3-phenyl] | ![4-(CONH-piperidine-N-CO2CH2CH3)-phenyl] | — | Colorless non-crystalline powder | 573 | 1.24(t, 3H), 1.30–1.60(m, 2H), 1.70–2.20(m, 2H), 2.70–3.10 (m, 2H), 3.68(s, 3H), 3.77(s, 3H), 3.90–4.30(m, 5H), 5.90–6.10 6.40–6.55(each br, d, 1H), 6.60–6.90(m, 4H), 6.90–7.40(m, 7H), 7.40–7.80 (m, 3H), 8.58(br, s, 1H) |

Test Example 1

With respect to the compound (1) according to the present invention, the pharmacological effects were tested. The results are as follows.

i) Test for inhibitory activity against ACAT using J774 cells:

The ACAT activity of J774 cells was measured as the radioactivity of cholesteryl oleate produced from [¹⁴C]oleic acid and cholesterol which were added to a culture solution.

More specifically, cultured J774 cells were plated on a 24F culture plate containing a serum-free RPMI 1640 medium so as to account for 1×10⁶ cells/well. Added to the cells were [¹⁴C]oleic acid, delipidized BAS (bovine serum albumin), reconstituted ribosome (0.3M glucose solution containing cholesterol and phosphatidylcholine at a weight ratio of 2:1) and 25-hydroxycholesterol to culture the cells for 4 hours at 37° C. under 5% CO₂. After the culturing, the cultured cells were disrupted with a 1% SDS (sodium lauryl sulfate) solution, and the lipid in the disrupted solution was extracted with hexane. The extract was dried to solid under reduced pressure. After the resultant residue was then developed (developing solvent: diethyl ether/hexane/acetic acid= 80/20/1) by TLC (thin-layer chromatography), the amount of cholesteryl oleate formed was determined by an imaging plate.

A DMSO (dimethyl sulfoxide) solution of each specimen was added in an amount of 1% to the culture solution to find its inhibition rate against the enzymatic activity in comparison with a DMSO control.

TABLE 15

| Compound | Inhibition rate against ACAT activity in J774 cells (%) |
|---|---|
| Compound 3 | 77.82 ± 4.00 |
| TMP-153 | 36.94 ± 11.93 |
| Dup 128 | 66.37 ± 6.17 |

Tested on 100 nM of each compound. (Mean ± S.D.; n = 3)
TMP-153 [H. Tawada et al., J. Med. Chem., 37, 2079–2084 (1994)]

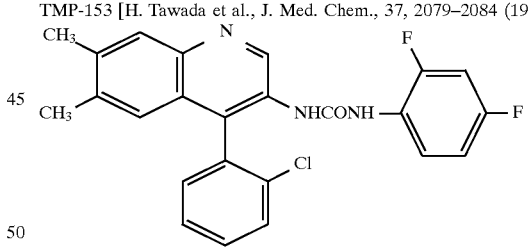

Dup 128 [T. P. Maduskuie, Jr., et al., J. Med. Chem., 38 1067–1083 (1995)]

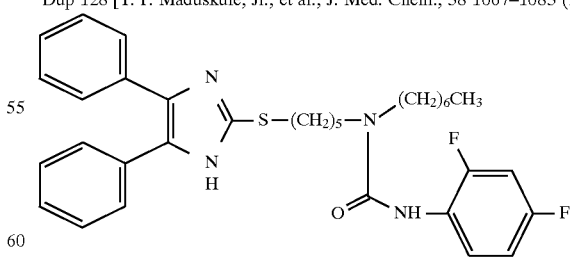

ii) Test for inhibitory activity against ACAT using rat liver microsome:

The ACAT activity of rat liver microsome was measured as the radioactivity of cholesteryl oleate produced from [¹⁴C]oleoyl-CoA and endogenous cholesterol.

More specifically, [$^{14}$C]oleoyl-CoA and delipidized BSA were added to a rat liver microsome fraction prepared in accordance with a method known per se in the art to conduct a reaction at 37° C. for 5 minutes. After the reaction, the lipid in the reaction mixture was extracted with hexane, and the extract was dried to solid under reduced pressure. After the resultant residue was then developed (developing solvent: diethyl ether/hexane/acetic acid 80/20/1) by TLC, the amount of cholesteryl oleate formed was determined by an imaging plate. A DMSO solution of each specimen was added in an amount of 1% to the reaction mixture to find its inhibition rate against the enzymatic activity in comparison with a DMSO control.

TABLE 16

| Compound | Inhibition rate against ACAT activity in rat liver microsome (%) |
| --- | --- |
| Compound 3 | 7.87 ± 9.26 |
| TMP-153 | 82.29 ± 2.79 |
| Dup 128 | 79.32 ± 7.01 |

Tested on 100 nM of each compound. (Mean + S.D.; n = 3)

As apparent from the results of the tests i) and ii), the compound (1) according to the present invention has still stronger inhibitory activity against ACAT in the mouse macrophage-like cells than against ACAT in the liver microsome. This fact means that the compound according to the present invention directly reduces the accumulation and storage of cholesterol esters in the artery wall to prevent the formation or development of atherosclerosis lesion. Therefore, such a compound is useful in preventing and treating arteriosclerosis, and moreover various diseases related thereto, for example, cerebral infarction, transient ischemic attack, angina pectoris, peripheral thrombus and peripheral occlusion.

As described above, the compounds (1) according to the present invention selectively and strongly inhibit ACAT in macrophages and are hence useful as prophylactic and therapeutic agents for arteriosclerosis.

What is claimed is:

1. A substituted vinylurea compound having the formula (I):

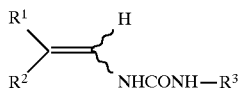

wherein:

$R^1$ is phenyl which is optionally substituted by 1 to 3 substituents selected from the group consisting of halogen, halogenated $C_{1-6}$ alkyl, $C_{1-6}$ alkoxy, amino, mono-$C_{1-6}$-alkylamino, di-$C_{1-6}$-alkylamino, hydroxyl, $C_{7-16}$ arylalkyloxy, methylenedioxy, cyano, benzoyl, $C_{2-7}$ alkanoyl, carbamoyl, carboxyl, $C_{1-6}$ alkoxy-carbonyl, $C_{1-6}$ alkoxy-methoxy, $C_{2-7}$ alkanoyloxy, nitro, sulfonic, sulfonamide, thiol, $C_{1-6}$ alkylthio, $C_{1-6}$ alkylsulfinyl, $C_{1-6}$ alkyl-sulfonyl, $C_{1-6}$ alkyl, $C_{2-7}$ alkanoylamino, benzoylamino, hydroxy-$C_{1-6}$-alkyl, carboxy-$C_{1-6}$-alkyl, $C_{2-6}$ alkenyl, $C_{2-7}$ alkanoyl-piperazinyl, $C_{1-6}$ alkyl-aminocarbonylpiperazinyl, $C_{2-7}$ alkanoyl-aminomethyl, $C_{1-6}$-alkylamino-carbonyl-$C_{1-6}$-alkyl, $C_{1-6}$ alkyl-ureidomethyl, and N-$C_{1-6}$-alkoxy-carbonylpiperadinylcarbamoyl;

$R^2$ is phenyl which is optionally substituted by 1 to 3 substituents as defined for $R^1$, or $C_{3-7}$ cycloalkyl; and $R^3$ is phenyl which is substituted by 1 to 3 substituents selected from the group consisting of halogen, halogenated $C_{1-6}$ alkyl, amino, mono-$C_{1-6}$-alkylamino, di-$C_{1-6}$-alkylamino, hydroxyl, $C_{7-16}$ aralkyloxy, cyano, benzoyl, $C_{2-7}$ alkanoyl, carbamoyl, carboxyl, $C_{1-6}$ alkoxy-carbonyl, $C_{1-6}$ alkoxy-methoxy, $C_{2-7}$ alkanoyloxy, nitro, sulfonic, sulfonamide, thiol, $C_{1-6}$ alkylthio, $C_{1-6}$ alkylsulfonyl, $C_{1-6}$ alkylsulfonyl, $C_{1-6}$ alkyl, $C_{2-7}$ alkanoylamino, benzoylamino, hydroxy-$C_{1-6}$-alkyl, carboxy-$C_{1-6}$-alkyl, $C_{2-6}$ alkenyl, $C_{2-7}$ alkanoyl-piperazinyl, $C_{1-6}$ alkyl-aminocarbonylpiperazinyl, $C_{2-7}$ alkanoyl-aminomethyl, $C_{1-6}$-alkyl-aminocarbonyl-$C_{1-6}$-alkyl, $C_{1-6}$ alkyl-ureidomethyl, and N-$C_{1-6}$-alkoxy-carbonyl piperadinylcarbamoyl, and wherein wave lines indicate that the bonding configuration is either E or Z; or a salt thereof.

2. The substituted vinylurea compound of claim 1, wherein $R^1$ is unsubstituted phenyl.

3. The substituted vinylurea compound of claim 1, wherein $R^1$ is phenyl substituted by 1 to 3 of said substituents.

4. The substituted vinylurea compound of claim 1, wherein $R^1$ is phenyl substituted by 1 to 3 substituents selected from the group consisting of halogen, $C_{1-6}$ alkyl, $C_{1-6}$ alkoxy, nitro, hydroxyl, methylenedioxy, mono-$C_{1-6}$-alkylamino, di-$C_{1-6}$-alkylamino, amino and carboxyl.

5. The substituted vinylurea compound of claim 4, wherein $R^1$ is phenyl substituted by 1 to 3 substituents selected from the group consisting of fluorine, methyl, isopropyl, methoxy, methylenedioxy, hydroxyl and dimethylamino.

6. The substituted vinylurea compound of claim 1, wherein $R^2$ is unsubstituted phenyl.

7. The substituted vinylurea compound of claim 1, wherein $R^2$ is phenyl substituted by 1 to 3 substituents selected from the group consisting of halogen, $C_{1-6}$ alkyl, $C_{1-6}$ alkoxy, nitro, hydroxyl, methylenedioxy, mono-$C_{1-6}$-alkylamino, di-$C_{1-6}$-alkylamino, amino and carboxyl.

8. The substituted vinylurea compound of claim 7, wherein $R^2$ is phenyl substituted by 1 to 3 substituents selected from the group consisting of fluorine, methyl, isopropyl, methoxy, methylenedioxy, hydroxyl and dimethylamino.

9. The substituted vinylurea compound of claim 1, wherein $R^3$ is phenyl substituted by 1 to 3 substituents selected from the group consisting of halogen, $C_{1-6}$ alkyl, $C_{1-6}$ alkoxy, nitro, hydroxyl, methylenedioxy, mono-$C_{1-6}$-alkylamino, di-$C_{1-6}$-alkylamino, amino and carboxyl.

10. The substituted vinylurea compound of claim 9, wherein $R^3$ is phenyl substituted by by 1 to 3 substituents selected from the group consisting of fluorine, methyl, isopropyl, methoxy, methylenedioxy, hydroxyl and dimethylamino.

11. The substituted vinylurea compound of claim 1, wherein $R^2$ is phenyl substituted by 1 to 3 substituents selected from the group consisting of cyclopropyl, cyclobutyl, cyclopentyl and cyclohexyl.

12. The substituted vinylurea compound of claim 11, wherein $R^2$ is phenyl substituted by 1 to 3 substituents slected from the group consisting of cyclopentyl and cyclohexyl.

13. A pharmaceutical composition for prophylactically and therapeutically treating arterial sclerosis, which comprises:

a) one or more compounds of claim 1, or a salt thereof; and b) a pharmaceutically acceptable carrier.

14. A method of preventing and treating arterial sclerosis, which comprises administering an effective amount of one or more compounds of claim 1, or a salt thereof to a patient in need thereof.

UNITED STATES PATENT AND TRADEMARK OFFICE
CERTIFICATE OF CORRECTION

PATENT NO. : 5,866,609

DATED : February 2, 1999

INVENTOR(S): Yoshihiko Kanamaru, et al.

It is certified that an error appears in the above-identified patent and that said Letters Patent is hereby corrected as shown below:

Column 34, Line 6 "$C_{1-6}$ alkylsulfonyl, $C_{1-6}$ alkylsulfonyl," should read
--$C_{1-6}$ alkylsulfinyl, $C_{1-6}$ alkylsulfonyl,--.

Signed and Sealed this

Twenty-first Day of September, 1999

Attest:

Q. TODD DICKINSON

*Attesting Officer*   *Acting Commissioner of Patents and Trademarks*